(12) United States Patent  (10) Patent No.: US 8,236,236 B2
Garner  (45) Date of Patent: Aug. 7, 2012

(54) METHOD OF STERILIZING

(75) Inventor: Christopher John Garner, Annapolis, MD (US)

(73) Assignee: UV03, Inc., Annapolis, MD (US)

( * ) Notice: Subject to any disclaimer, the term of this patent is extended or adjusted under 35 U.S.C. 154(b) by 223 days.

(21) Appl. No.: 12/528,266

(22) PCT Filed: Feb. 20, 2008

(86) PCT No.: PCT/US2008/054400
§ 371 (c)(1),
(2), (4) Date: Oct. 16, 2009

(87) PCT Pub. No.: WO2008/103715
PCT Pub. Date: Aug. 28, 2008

(65) Prior Publication Data
US 2010/0047116 A1    Feb. 25, 2010

Related U.S. Application Data

(60) Provisional application No. 60/902,502, filed on Feb. 22, 2007.

(51) Int. Cl.
*A61L 2/24* (2006.01)
*B01J 19/08* (2006.01)
(52) U.S. Cl. .................................. 422/3; 422/186.07
(58) Field of Classification Search .......... 422/3, 186.07
See application file for complete search history.

(56) References Cited

U.S. PATENT DOCUMENTS

| 4,915,435 | A | 4/1990 | Levine |
| 4,990,311 | A | 2/1991 | Hirai et al. |
| 5,225,167 | A | 7/1993 | Wetzel |
| 5,330,722 | A | 7/1994 | Pick et al. |
| 6,156,267 | A * | 12/2000 | Pai et al. ............................. 422/3 |
| 6,613,277 | B1 | 9/2003 | Monagan |
| 2003/0086813 | A1 * | 5/2003 | Fleischer ........................... 422/3 |
| 2003/0230477 | A1 | 12/2003 | Fink et al. |
| 2004/0047776 | A1 | 3/2004 | Thomsen |

(Continued)

FOREIGN PATENT DOCUMENTS

CA    2602230 A1    9/2005

(Continued)

OTHER PUBLICATIONS

Korean Intellectual Property Office, International Search Report for International Application No. PCT/US2008/054400 dated Jul. 8, 2008, 2 pages.
A Dyas, BJ Boughton, BC Das, "Ozone killing action against bacterial and fungal species; microbiological testing of a domestic ozone generator," Departments of Microbiology and Haematology, Queen Elizabeth Hospital, J. Clin. Pathol. 1983; 36:1102-1104.

(Continued)

*Primary Examiner* — Kevin Joyner
(74) *Attorney, Agent, or Firm* — Fitch, Even, Tabin & Flannery, LLP

(57) ABSTRACT

A bio-air sterilization system and method of use thereof is provided that can remove and render benign harmful contaminants and particulates, such as bacteria, viruses, and molds, from air within an enclosed area, as well as, in principle, from the exposed surfaces located within the enclosed area. In one aspect, the sterilization system includes a self contained, mobile sterilization unit that includes at least an ultraviolet array, an air flow control mechanism for diverting the air flow within the system through either a filter or through an ozone removal zone, an ozone generator, and a blower apparatus to pull the air through the system and out through ports, such as a nozzle system, to the surrounding environment.

14 Claims, 9 Drawing Sheets

U.S. PATENT DOCUMENTS

| | | |
|---|---|---|
| 2005/0186108 A1 | 8/2005 | Fields |
| 2007/0154344 A1* | 7/2007 | Choi et al. .................. 422/3 |
| 2008/0031770 A1 | 2/2008 | Heselton et al. |
| 2008/0213125 A1 | 9/2008 | Boast et al. |
| 2010/0178196 A1 | 7/2010 | Garner |

FOREIGN PATENT DOCUMENTS

| | | |
|---|---|---|
| EP | 1 023 224 B1 | 1/2006 |
| EP | 1 175 230 B1 | 1/2007 |
| WO | 2008014615 A1 | 2/2008 |

OTHER PUBLICATIONS

W.J. Kowalski, W.P. Bahnfleth, B.A. Striebig, T.S. Whittam, "Demonstration of a Hermetic Airborne Ozone Disinfection System: Studies on *E. coli*," AIHA Journal (64:222-227), Mar./Apr. 2003, Copyright 2003, American Industrial Hygiene Association.

Korean Intellectual Property Office International Search Report and Written Opinion for International Application No. PCT/US2008/054406 dated Jun. 30, 2008 (9 pages).

* cited by examiner

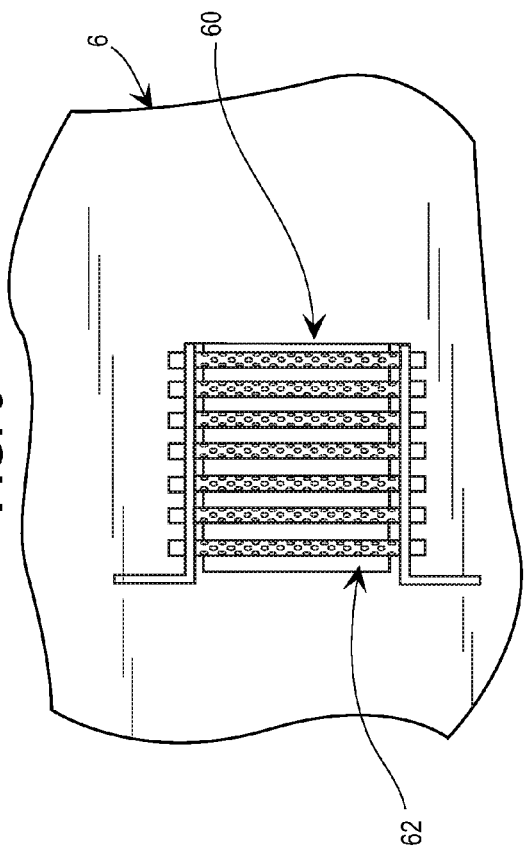
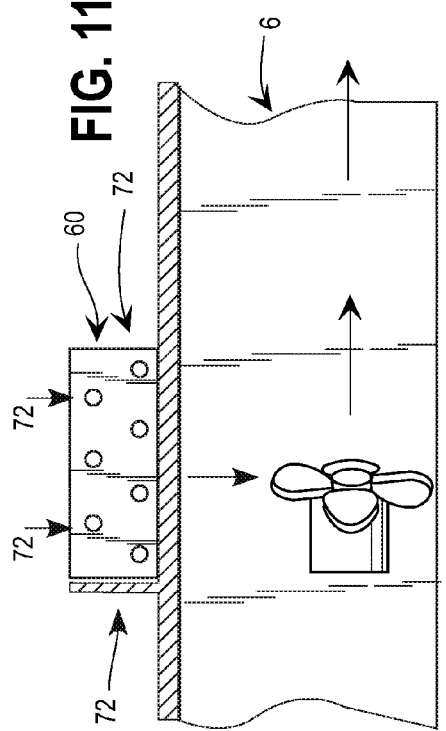
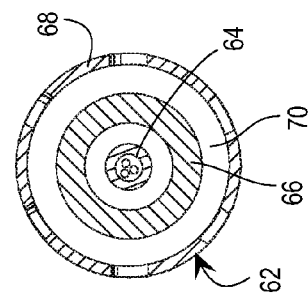

METHOD OF STERILIZING

CROSS-REFERENCE TO RELATED APPLICATIONS

This application is a U.S. national phase application filed under 35 U.S.C. §371 of International Application PCT/US2008/054400, filed on Feb. 20, 2008, designating the United States, which claims benefit of U.S. Provisional Application No. 60/902,502, filed Feb. 22, 2007, which are hereby incorporated herein by reference in their entirety.

FIELD OF THE INVENTION

The present invention relates to an air filtration and cleaning system and, in particular, to an air sterilization unit and related methods for removing harmful biological contaminants and particulates from an enclosed area.

BACKGROUND OF THE INVENTION

It has been a long-standing goal in the field of air filtration systems to remove harmful contaminants and particulates, such as bacteria, viruses and molds, from air within an enclosed area, as well as from the surfaces located within the enclosed area, thus maintaining a safe workplace for individuals.

People spend about 75 to about 90 percent of their time indoors where they are exposed to a growing number of health-threatening indoor pollutants. These pollutants can be categorized into three groups: biological contaminants, such as bacteria, viruses, and molds; toxic gases and fumes given off by furniture, carpeting, etc.; and particulates, such as dust and smoke. Approximately half of the major office buildings have contaminated heating, ventilation, and air conditioning (HVAC) systems. If not properly maintained, the HVAC systems are a hotbed for the growth of molds and bacteria, regardless of the age of the building. Occupants of these buildings can be expected to suffer from symptoms related to exposure to these health-threatening indoor pollutants. The problem of health-threatening indoor pollutants is exacerbated when the building is a health facility where not only are there a greater number of harmful health-threatening pollutants present, but occupants of the health facility may be more susceptible to maladies caused by these health-threatening pollutants.

A known solution for removing harmful contaminants from ambient air is the use of air purifiers. Air purifiers use a scientifically advanced process that combines the power of germicidal ultraviolet (UV) light, purifying hydroxyl, activated oxygen, and photo-ionization for purifying air and sanitizing an area. However, existing air purifiers do not use the multiple approach of pre-ionization of the incoming air, high efficiency particulate (HEPA) filtration, and sterilization by use of ultraviolet nm lamps for a more complete solution. Further, most existing air purifiers use small ultraviolet lamps that do not allow adequate time required for sterilization.

Another approach for removing harmful contaminants from surfaces is the use of chlorine to clean water and surfaces. However, chlorine may leave harmful residuals within the drinking water and chlorine also cannot be readily generated on site. The chlorine must be shipped to the site from manufacturers located a distance away from the point of need. During emergency situations, proper handling of chlorine containers may be impractical.

Ozone has been used in municipal drinking water systems to purify and kill microorganisms and bacteria. Ozone, however, is a powerful oxidant and its exposure to humans generally needs to be limited. The U.S. Occupational Safety and Health Administration limits ozone exposure in the workplace to less than 0.1 ppm over an 8 hour period. When used to purify fluids, however, reduction to acceptable levels is generally not a concern because ozone has a half-life of about 8 to about 30 minutes in water (depending on temperature). Therefore, any ozone used to purify municipal drinking water will have decayed to acceptable levels long before it is exposed to human consumption. Use of ozone to sterilize an enclosed air space presents other challenges because the half-life of ozone in air can be as high as about 36 to about 72 hours (depending on temperature). Therefore, if ozone is used to sterilize an enclosed area, depending on the concentration used to sterilize that area, the space may not be suitable for human contact for over a day and a half.

Attempts have been made to sterilize rooms using ozone generation, such as hospital size rooms and larger (i.e., about 1000 $ft^3$ or larger), but such previous attempts have either used large, fixed systems or have not been able to generate sufficient concentrations of ozone to kill any detectable levels of contaminates. Large, fixed systems only sterilize the room to which they are fixed and provide no sterilization to rooms that are not associated with the ozone. Therefore, fixed systems require multiple, expensive systems and increased capital and operating costs. Prior systems have also been ineffective at providing sufficient levels of detectable biocide activity using airborne ozone in hospital sized rooms.

Notwithstanding these and other proposals, a need remains for a sterilization system, especially a mobile system, that effectively provides the user with an ability to sterilize an ambient environment, such as a patient room or mobile operating room in a turnkey manner. In particular, a need remains for a mobile system for filtering out particulates, safely destroying biological contaminants such as by ozone generation, effectively converting the ozone to highly ionized ambient air, and providing for the convenient, efficient removal of the ozone from the environment about the mobile system.

SUMMARY AND OBJECTS OF THE INVENTION

These and other objectives are met by the present system that provides a bio-air sterilization system, that can remove and render benign harmful contaminants, pathogens, and particulates, such as bacteria, viruses, and molds, from air within an enclosed area, as well as, in principle, from the exposed surfaces located within the enclosed area. It is preferred that the sterilization system is capable of providing sufficient sterilization to remove and render benign harmful contaminates and particulates in an enclosed area, such as a hospital sized room, which can be, in some cases, greater than about 1000 $ft^3$ or, in other cases, greater than about 2000 $ft^3$. However, the systems described herein will also sterilize smaller rooms and enclosures.

In one aspect, the sterilization system includes a self-contained, mobile sterilization unit that includes an air intake, a filter for the air (preferably a HEPA filter), an ultraviolet array, an air flow control mechanism for diverting the air flow within the system through either an additional filter (preferably a HEPA filter) or through an ozone removal zone, a further filter, an ozone generator, a blower apparatus to pull the air through the system and out through ports, such as a nozzle system, to the surrounding environment. Since the blower apparatus pulls air into the sterilizer system, the sterilization function can be maintained on a continuous duty cycle, or other duty cycle, for a period of time, especially a pre-determined selected period of time, when the air circulating within the system is not diverted through an ozone removal zone. When ozonated air is diverted through the ozone removal zone, the ozone generator is preferably off-line.

In another aspect of the system, a method for sterilizing an environment utilizing a self-contained mobile sterilization unit includes operating a sterilization system in the environment to be sterilized for such period of time as desired to achieve sterilization or the desired degree of sterilization. By one approach, the method includes transporting a self-contained mobile sterilization unit to a predetermined space; drawing an air flow into the mobile unit; optionally, exposing the air flow to ultraviolet radiation having a maximum disinfecting level up to and including the ability to kill tuberculosis and/or hepatitis A; and dosing an amount of ozone to the air flow sufficient to provide ozone concentration to the predetermined space to sterilize the predetermined space. In one case, the amount of ozone can be dosed up to about 1 gram per hour (in other cases, up to about 10 grams per hour). In another case, the ozone can be maintained up to about 20 ppm (in other cases, about 1 to about 10 ppm) for a predetermined time, such as, but not limited to, up to about 8 hours (generally about 1 to about 2 hours and in some cases about 30 minutes or less). It will be appreciated the ozone dosing amounts, exposure duration, and concentration levels can vary depending on the contaminants to be removed, size of the enclosed space, environmental parameters, and other factors. After the predetermined exposure duration, the ozone is removed from the enclosed space. After such sterilization cycle is complete, the mobile sterilization unit can be removed from the space.

In another aspect of the system, a method of measuring and controlling the application of ozone is provided that is particularly useful for a self-contained, mobile sterilization system. By one approach, the method includes first measuring an environmental parameter, such as, but not limited to, temperature (wet or dry bulb), relative humidity, pressure, dew point, other psychrometric parameters, or combinations thereof. Next, a particular agent or contaminant to be sterilized is selected. The agent or contaminant can include, for example, various bacteria, mold, virus, fungi, other contaminants, and combinations thereof. After measuring the environmental parameter and selecting the agent, the minimum ozone dosage and minimum application duration are determined based on the environmental parameters and agent. If needed, the various environmental parameters can be adjusted (i.e., adjusting temperature, humidity, and the like) to modify the dosage or application time. Then, a concentration of ozone per unit time factor (i.e., ppm-minute) is determined that is sufficient based on the space to be sterilized, environmental parameters, and selected agent(s) and/or contaminant(s) to kill such agents or contaminants. During the dosing exposure duration, the concentration of ozone (or environmental parameter) can be continuously monitored (i.e., every 10 seconds, every minute, every 5 minutes, etc.) and the dosing rate (or environmental parameter) can be adjusted based on the measured concentration (or measured environmental parameter) in order to generally maintain the concentration of ozone per unit time.

BRIEF DESCRIPTION OF THE FIGURES

FIG. 9 shows an exemplary ozone generating element, such as a plasma pack.

FIG. 10 is an exemplary anode and cathode arrangement in the ozone generating element.

FIG. 11 is an exemplary arrangement of an exemplary ozone generating element and blower fan.

DETAILED DESCRIPTION OF THE PREFERRED EMBODIMENT

Figure 1:
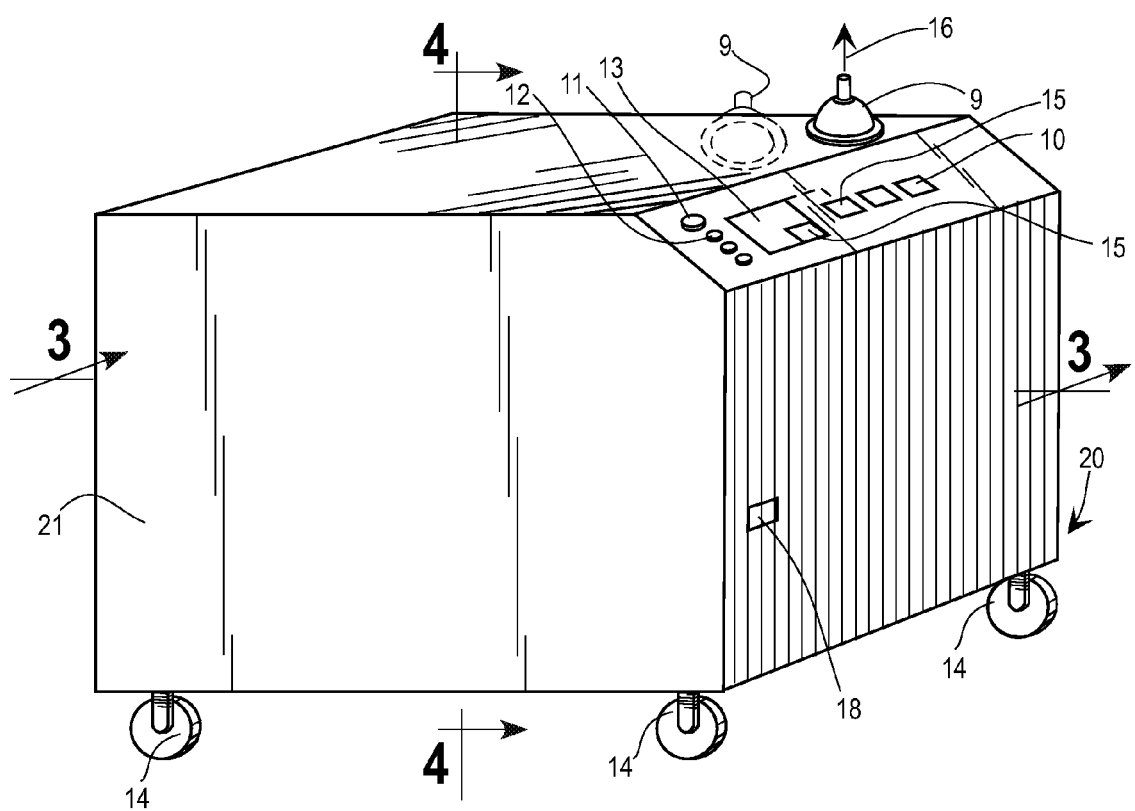
FIG. 1 is an illustration of one embodiment of the invention that is capable of being wheeled into an environment to be sterilized.

In a preferred embodiment, a self-contained, mobile sterilizer system 20 as generally illustrated in FIG. 1 is mounted on wheels 14, such as castors, to facilitate its being transportable and placed in position in an environment to be sterilized. As shown in FIG. 1, an embodiment of the sterilization system 20 has a front panel with a display 13, indicator elements 10, an on-off switch 11, and other display indicia or switches 12 (such as for manual override). The switch 11 can be a key operated switch or push button style switch. Display 13 can include a programmable logic controller 15 for the sterilization system, or the controller 15 can be a separate component, but is in operative connection with the display 13 and the components to be controlled in the sterilization system 20. Display 13 can comprise a touch screen. The sterilization system 20 has a closed housing with a pair of exit ports 16 shown as nozzle(s) 9 and an intake 17 for air through a filter 1 (see FIG. 2 and FIG. 3). Although a pair of nozzles 9 is shown in FIG. 1, the actual number of nozzles 9 is not restricted to that number. One of the nozzles 9 is shown in FIG. 1 as being on a side panel to sterilization system 20 to indicate that location is not restricted. Thus, for instance, it will be appreciated that nozzles can be positioned side-by-side on the top surface. Electrical power cord(s), electrical outlets, light sockets, wiring, internal electrical connections and the like are not shown and it is understood that these can be positioned and located consistent with a particular design as will be appreciated by a person skilled in the art based on this application. It will be appreciated that access panels can be provided, such as in the top surface and or on the side, back, and/or front panels of the sterilization system 20, to permit access to components within the housing for service and/or replacement (for example, elements in UV array, filters, etc.).

The preferred mobile sterilizer system 20 includes at least two functions and several modes. In general, such a system 20 may have at least three modes. The general functions are to sterilize a room using ozone alone or using a combination of ultraviolet light and ozone as disinfecting agents, or optionally with an ion generator (such as a so-called hydroxyl generator). To this end, the mobile system 20 may include in a single, transportable housing 21 an ozone generator 6, an ultraviolet light source 2, and an optional hydroxyl generator 10. It will be appreciated that the Figures illustrate various arrangement of these components in the housing 21. Such arrangements are only exemplary and can vary as needed for a particular situation.

Ozone is a powerful gaseous chemical that can destroy all germs when used in proper dosages. Ozone can be used as a disinfectant of choice to sterilize a room. Ozone is a noxious material. Ozone is thus preferably used for such purpose when the room is unoccupied. Since ozone is a gas, it can penetrate most areas within a room and kill surface and airborne bacteria, mold, or viruses. While ozone can sterilize a room via air application, it is most commonly used as a sterilizing agent in the water treatment industry. Heretofore, ozone has not apparently not been regarded as disinfectant characterized as having utility in atmospheric sterilization because of concerns associated with gases, namely as a gas ozone becomes unwieldy in open environments and can disperse too rapidly.

One of the advantages of the mobile sterilizer system 20 is its ability to be transported to an enclosed space and sterilize the enclosed space, such as a hospital sized room of about 1000 ft$^3$ or larger (preferably, about 2000 ft$^3$ or larger), and also cleanse the space of ozone after the space is subjected to ozone treatment. The application or dosing of the room can be selected and visually displayed, such as with the display 13 with user inputs, and controlled such as by programmable means, such as the programmable logic controller 15, to set the dosing and duration of dosing (ozone generation), as well as de-ozonation, and, if desired the operation of the UV array. For example, an integrated timer in the programmable logic controller can be used to customize control of the ozone generator's period of operation. The sterilization system 20 can, if desired, be fitted with a motion sensor 18 (FIG. 1) that de-activates the ozone generator 6 if someone should enter the enclosed area. It will be appreciated that any alarm or notification means can be provided, such by an electronic connection to a network or other computer/communications system to alert the operator, which can include signal transmission to a remote receiving device such as a telephone (VOIP, cell, landline, etc.) or paging device. The signal transmission for notification is not limited and includes e-mail notification and so-called instant or text messaging, among others. Electronic connection includes wireless. An audible alarm or visual alarm can also be provided, such as to signal when de-ozonation is completed. While display and programmable means may be presently preferred, a manual system can, in principle, be used as well.

The ozone removal is accomplished in an ozone removal zone 4. The ozone removal zone 4 can comprise a catalytic filter element, an ionized gas generator, and/or an electromagnetic radiation generator contained within the housing 21 of the system 20 to thereby promote an efficient, effective method to destroy the ozone and remove it from the room in a short amount of time so that the room can be quickly re-occupied. Preferably, ozone is removed from the enclosed space in about 2 hours or less and, in some cases, in about 30 to about 60 minutes. By one approach, available information indicates that the ozone removal zone 4 is configured to reduce the concentration in the enclosed space to about 0.1 ppm or less in the removal time. It will be appreciated that removal of ozone can vary depending on the concentration, room size, and other factors.

The system 20 can also have the ultraviolet light source 2, which can include a plurality of ultraviolet lamps. For instance, in one embodiment, the ultraviolet light source 2 is comprised of an array of ultraviolet lamps emitting light at about 254 nanometers wavelength, which can provide a powerful disinfectant function. Other wavelengths may also be used as needed. The science of UV light disinfecting is well known. There are many manufacturers of UV bulbs. They have established dosing levels for UV light. UV lamps and their general attributes are described in a publication from Phillips, US Purification—Application Information, Perfection Preserved (Phillips), the complete disclosure of which is incorporated herein by reference. The UV light source can be chosen and designed to have a minimum disinfecting level of up to and including the ability to kill tuberculosis and/or Hepatitis A. The UV light source can be operated in combination with the ozone subsystem or independently of the ozone portion of the system. The UV light source is within the housing for the sterilization system and in one embodiment may function to kill certain airborne pathogen contaminates, and thus may be operated even if the sterilization system 20 is located in a room that is occupied.

The sterilization system 20 can operate using the ultraviolet array having sufficient emission to disinfect air circulating within the system in combination with the internal ozone generator 6. In principle, there may be a synergistic effect obtained when using ozone and UV in combination as disinfecting agents simultaneously. For example, sterilization of the enclosed space may occur in less time.

Figure 2:
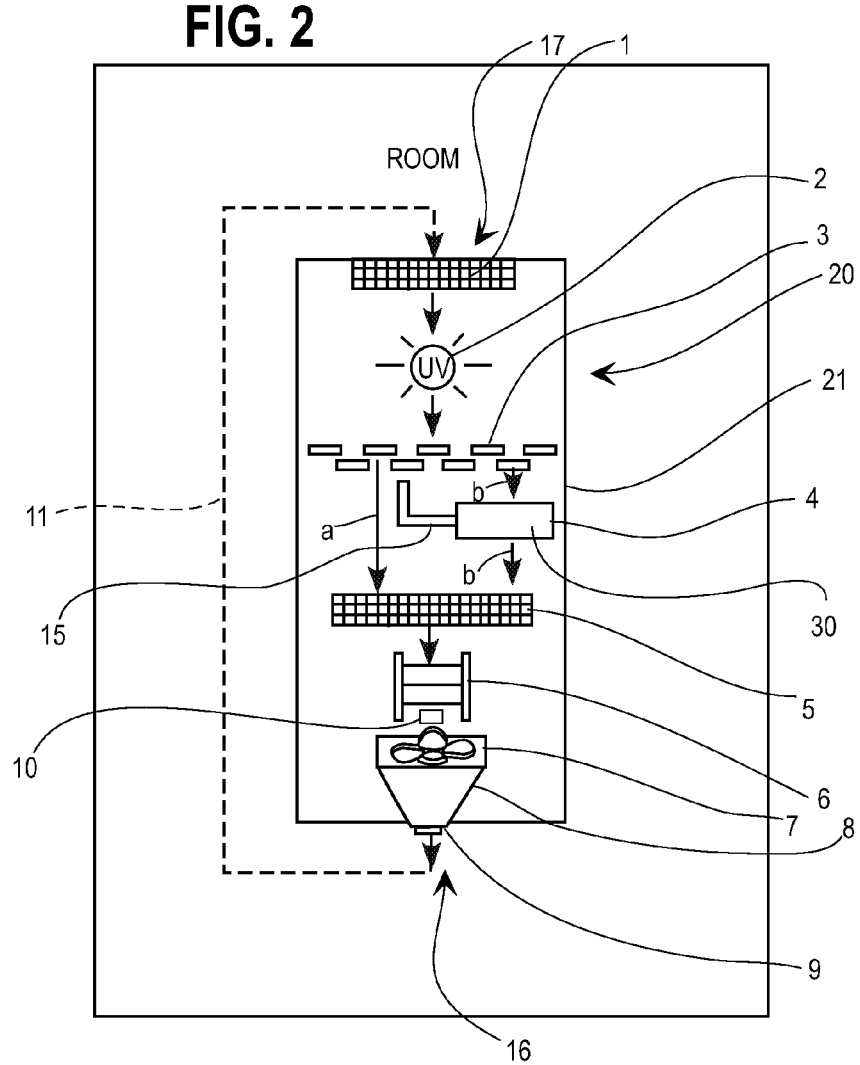
FIG. 2 illustrates air flow paths through an embodiment of the present invention with respect to certain elements of the exemplary sterilization system.
Figure 3:
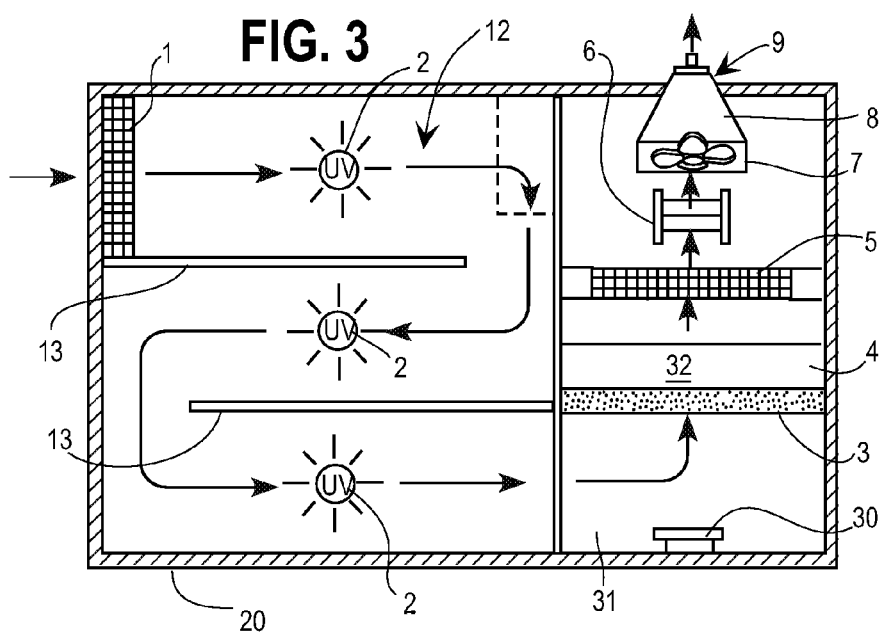
FIG. 3 is cross section along a horizontal axis of an embodiment of an exemplary sterilizer system.

As shown in FIG. 2, air 11 is the working fluid in the mobile, room sterilizer 20. The air path design is responsible for the ozone delivery to the room. Ozone introduced into a circulating air flow can be later removed as depicted when the circulating air is diverted to path "b" in FIG. 2. In FIG. 2, air enters the apparatus through a filter 1, sometimes called an intake filter. By preference, the filter 1 removes dust to protect a secondary or down stream filter 5 from becoming clogged and saturated with particulates. The filter 1 (and/or the filter 5) is preferably antimicrobial and can be treated to provide additional germicidal action, i.e., can help kill germs. Alternatively, filter 1 (and/or filter 5) can be a HEPA (High Efficiency Particulate Air) filter that is capable of removing, in some cases, up to at least 99.9 percent of airborne particulate down to about 0.3 microns in diameter. However, the efficiency of the HEPA filter may vary. Next, the air passes through the ultraviolet light source 2. By preference, the ultraviolet source 2 is designed to irradiate the air with a dosage of UV radiation effective at killing germs, including tuberculosis and Hepatitis A. As shown in FIG. 3, the light source 2 can be an array of three UV generators, although the numbers and orientation are not limited to the exemplary embodiment as shown. For instance, the array may have more than three UV generators in the light source 2.

As shown in FIG. 3, the ultraviolet light 2 in the sterilizer system 20 can be within a chamber 12 that is configured to allow the air to circulate past the UV lights with a sufficient dwell time to be exposed to the ultraviolet radiation whereby a combination of the UV light intensity plus time of exposure may be sufficient to extirpate the pathogen (germs, etc.) or at least provide a desired degree of sterilization. By preference, the air path meanders through said chamber 12 and there may be baffles 13 (not shown in FIG. 2, but see FIG. 3). The baffles 13 are preferably spatially disposed and shaped within said chamber 12 so that the air has a desired dwell time (duration of exposure to the UV), while preferably flowing at a relatively uniform velocity past through the ultraviolet light 2.

As shown in FIG. 2, the air flows through an air valve 3. The air valve 3 functions as a diverter valve directing the air directly either via path "a" thence to filter 5 and to the ozone generator 6 or via path "b" through a de-ozonation zone 7 (and presumably with the that may include a plenum 8 and is introduced into the environment via the nozzles 9 surrounding the sterilization system 20. When the sterilization system 20 is operational, a blower system 7 draws the air in through the intake filter 1, whereby a continuous flow of air can be obtained through the system. The blower system 7 is preferably sized to ensure appropriate metered air flow and circulation within the sterilization system 20, and thus it should preferably be such as to account for pressure drops because of air flow through the filters 1 or 5, through the de-ozonation zone 4, or around baffles 13 in the chamber 12 having the UV source 2 (so as to ensure a desired dwell time for exposure to UV), etc. In principle, the blower system 7 can be chosen so as to draw air through sterilization system 20 at a fixed speed, at selected or programmed speeds (bi-speed or three speed, as examples) or at a variables speed during operation. Air flow through the system 20 can range, for example, from about 60 to about 400 CFM. It will be appreciated, however, that such flow rates are exemplary and may vary depending on the particular system. Nozzle(s) 9 or other suitable structure can be in flow communication with the plenum 8 and can be used to direct the air, such as ozonated air, from the sterilization system 20 to the surrounding environment, such as into a room (for example, a bathroom, surgery room, recovery room, or the like), or to a region of a room, such as a corner.

The air valve 3 directs air flow directly into the filter 5 via air path "a" while being closed to air path "b" so as to prevent air being ozonated from passing through ozone removal zone 4. The air valve 3 can be actuated upon signal from the programmable logic controller 15 (not shown), which may have a manual override, to divert air to path "b".

Figure 5:
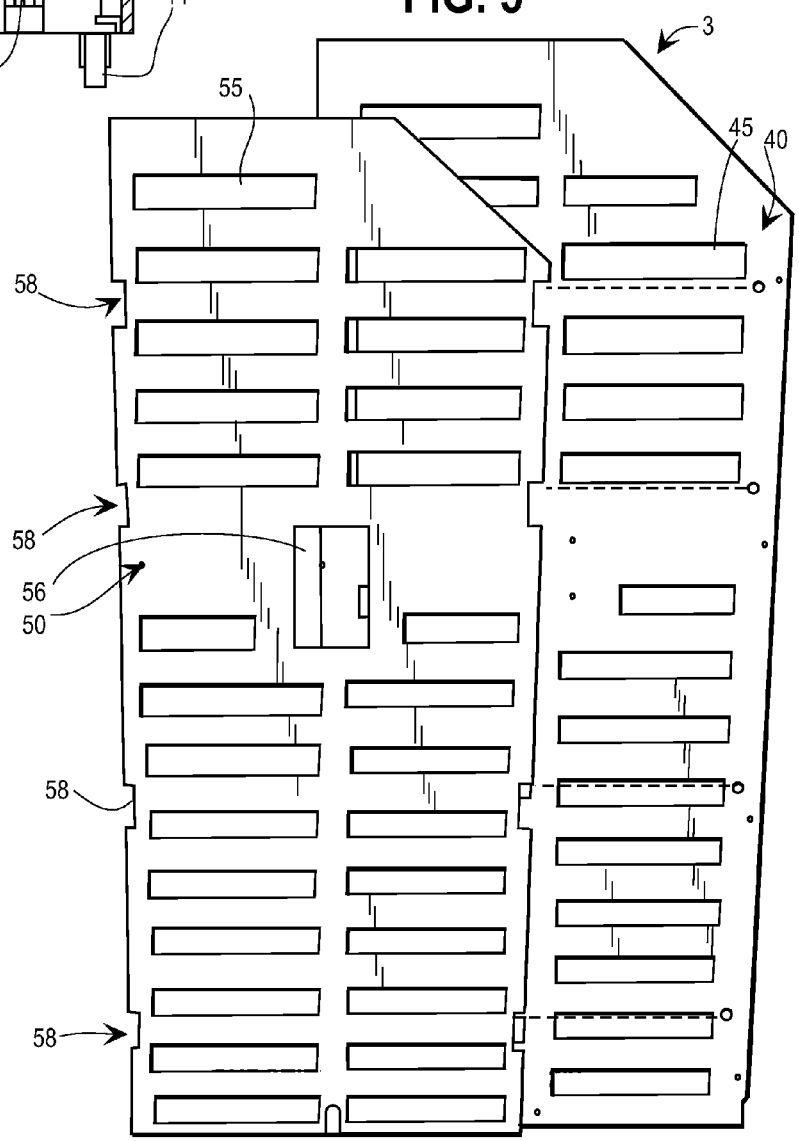
FIG. 5 shows partially overlaid louvered plates from an air valve in a disassembled form.
Figure 6:
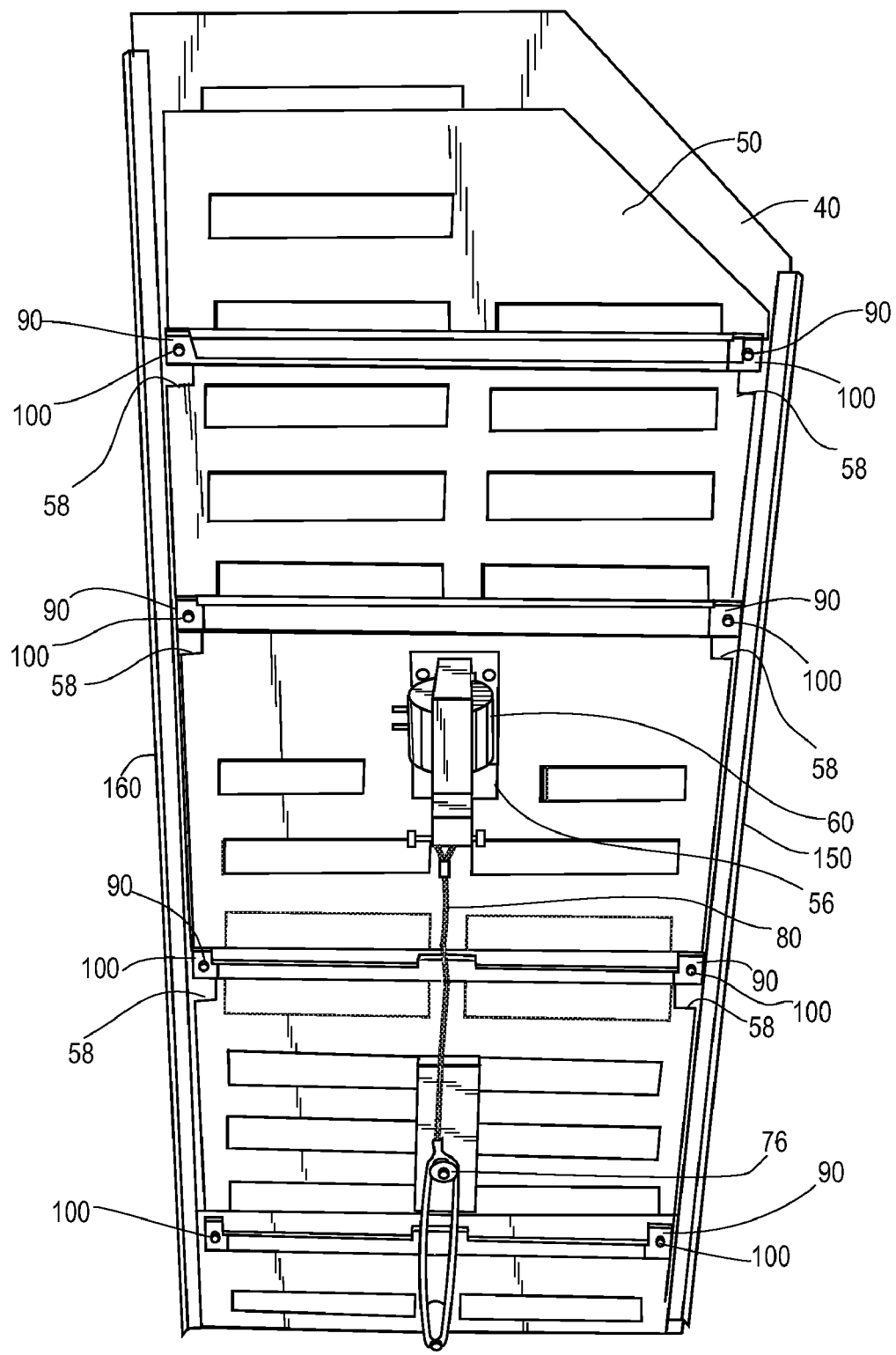
FIG. 6 shows an exemplary air valve.
Figure 7:
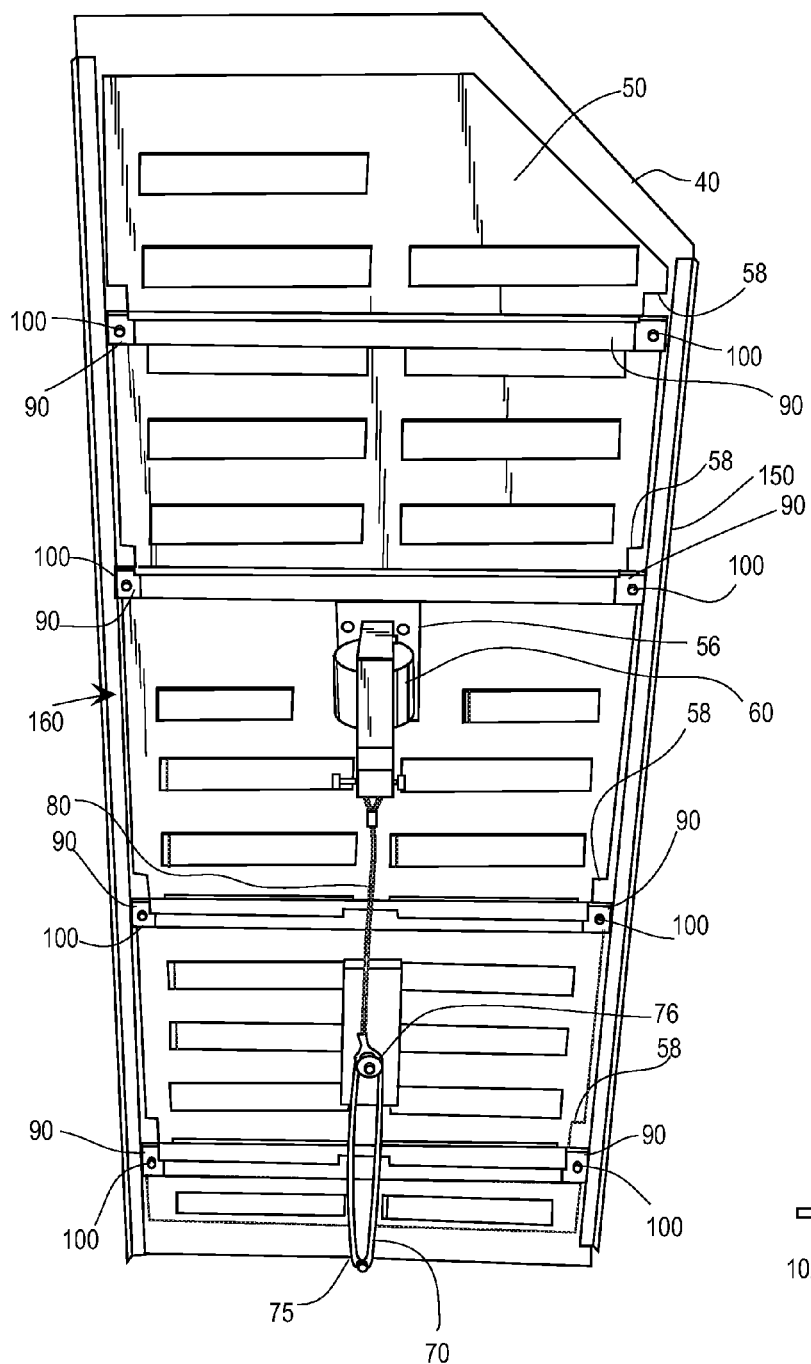
FIG. 7 shows an exemplary air valve in an actuated position.
Figure 8:
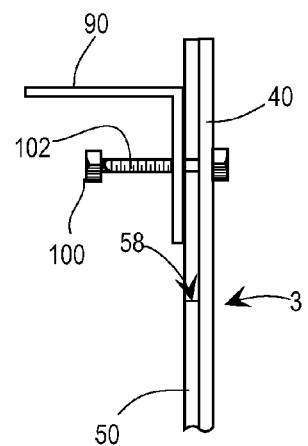
FIG. 8 shows in an edge view a cross member, a biased post, and parts of the valve plates in an exemplary air valve.

In one embodiment, the air valve 3 includes a stationary valve plate 40 in slideable engagement relative to a moveable valve plate 50 as seen in FIGS. 5-8. The valve plates 40 and 50 have louvers 45 and 55 that are arranged so that moveable slide plate 50 can be either stationary (at rest) or slid relative to the stationary valve plate 40. Thus, the respective louvers 45 and 55 in said plates 40 and 50 are positioned so that air flow is permitted in either of the above mentioned air flow paths in FIG. 2, but not both at the same time. This is illustrated in FIG. 5 that shows plate 50 partially overlying a plate 40 from a disassembled air valve 3. FIG. 6 shows said plate 50 overlying plate 40 to illustrate that air flow would be allowed via path "a", but not path "b" when plate 50 is at rest when actuator 60 is not actuating. FIG. 7 shows plate 40 manually slid upwardly relative to plate 50 to illustrate when the air valve 3 is fully actuated the air path "a" is closed and the air path "b" is opened. The rectangular cut out 56 in the center of plate 50 fits over the actuator 60 (FIGS. 6 and 7) that can be mounted on plate 40, but also is sized to allow play so plate 50 can be moved relative to plate 40 when actuator 60 is actuated. FIG. 8 shows a portion of an uninstalled exemplary air valve 3. An actuator 60 is used to actuate a suitable mechanism that slides the moveable valve plate 50 over the stationary valve plate 40. The actuator 60 can be a solenoid type system or other suitable apparatus that is capable of sliding (moving) plate 50 relative to plate 40 from a position where the respective louvers of such facing plates allow only air path "a" to be open to a second position whereby the louvers allow only air path "b" to be open.

As shown in FIG. 7, the actuator 60 may be linked to a biasing element 70, such as a spring, so that plate 50 returns to a first position when actuator 60 is no longer 'fired.' It will be appreciated that the biasing element 70 will have one end connected to plate 40 and the other end connected to plate 50 as in FIG. 7. The actuator 60 is preferably operatively controllable via the programmable logic controller 15 for the sterilization system 20. The actuator 60 is preferably operatively controlled by the controller 15 (programmable logic controller mentioned hereinabove), which may receive input from a sensor 30 (FIG. 3) to trigger the actuator 60, such as for activation or de-activation. For example, the actuator 60 may be automatically triggered to direct air to the ozone removal zone 4 upon the sensor 30 detecting the presence of a person in the room. It will be appreciated that the sensor 30 can additionally be used to monitor the ozone concentration during the ozonation step. Sensor 30 can be augmented or replaced by other sensors mounted, for instance, to sense the ozone concentration in the environment within which the sterilization system 20 is placed. Such other sensor or sensors can be mounted to be exposed on an exterior surface of the sterilization system 20.

The moveable valve plate 50 is preferably arranged and installed so one of its surfaces faces the incoming flow towards air flow valve 3. This orientation may enable the moveable plate 50 to better seal against the stationary plate 40 by taking advantage of the pressure differential created by the air flow. In addition to the valve 3 using the pressure differential to seal, the moveable valve plate 50 can be biased against the stationary plate 40. As shown in FIGS. 6 to 8, for example, pairs of members 100 can be provided with biasing means, such as a spring or torsion element 102 (FIG. 8), to bias plate 50 against plate 40. The members 100 fit within notched portions 58. Notches 58 are on both side edges of plate 50, with notches 58 on one such side shown in FIG. 5. An element 90 can be used to connect pairs of biased members 100 (studs or posts, or the like) to provide more uniform biasing and to help maintain plate 50 in slideable, facing, but sealed relationship to plate 40. The plates 40 and 50 may receive, if desired, a friction aid, preferably a long lasting, non-volatile, non-particulate lubricant. For instance, in principle, the plates may have their facing surfaces Teflon coated, as one example. By preference, in an exemplary embodiment, the moveable plate 50 is thinner than the stationary plate 40. The plates 40 and 50 can be made of metal, such as aluminum. It will be appreciated that this embodiment of the air valve 3 is merely illustrative as other means for providing air flow control between path "a" and path "b" will be apparent to a person skilled in the art in view of this specification.

The de-ozonation zone 4 comprises a de-ozonator 32, such as a filter as mentioned hereinabove. The filter may be comprised of, for example, manganese dioxide, manganese dioxide and copper oxide, or PPS fibers (polyphenylene sulfide fibers) sandwiched in a filter-like containment. An element 15 (i.e., baffle, wall, or other blockage) depicted in FIG. 2 can be elbow-shaped and it ensures that the de-ozonation zone is not open to air flowing along air path "a". The element 15 is not limited to an elbow-shape. Air flows through the de-ozonation zone 4 through path "b". By preference, the sterilization system 20 operates with air flowing along air path "a" during the ozonation stage and along air path "b" during the de-ozonation stage. Alternatively, the de-ozonator 30 may also include an electromagnetic ozone generator capable of generating discrete bands of electromagnetic radiation sufficient, in principle, to catalyze ozone or cause ozone to oxidize itself. While not wishing to be limited by theory, it is believed that some wavelengths greater than about 254 nanometers may be sufficient for the de-ozonator 4.

As shown in FIGS. 9 and 10, the exemplary ozone generator 6 can comprise a corona discharge ozone generator 60. The corona discharge ozone generator 60 makes use of a plurality of anode/cathode cells 62. The cells 62 include a concentric assembly of a central high voltage electrode 64, a ceramic dielectric 66 surrounding the electrode 64, and an outer perforated tube 68. Ozone is created when a gas (i.e., ambient air or oxygen) passes through a space 70 between the anode and cathode while a high voltage is applied across the anode and cathode arrangement. As the gas passes through the space 70 between the anode and cathode, the electric field created by the voltage applied to the anode and cathode splits some oxygen molecules, and the released oxygen atoms react with oxygen molecules to form ozone. In particular, the corona discharge pack 60 is constructed of a rolled stainless steel, perforated shell 68. A ceramic dielectric 66 is inserted into the shell and a working gap 70 is established between the ceramic dielectric 66 and the shell 68 to support the corona discharge. Commercial low voltage power is generally stepped-up to the high voltage necessary to create the corona by a frequency/voltage inverter (not shown) before delivery to the ceramic core. As it passes through the corona, the oxygen in ambient air becomes excited and its oxygen molecules become disassociated. Some of the oxygen molecules recombine into ozone. The corona discharge ozone generator 60 is designed to produce ozone levels adequate for the required room disinfection. For simplicity of description, the following description may also refer to a "second ultraviolet lamp" and it is understood that the corona discharge ozone generator 60 can be substituted for the second ultraviolet lamp. The corona discharge or so-called plasma ozone generator can be a high frequency system or a low frequency system.

The ozone generator 6 should be configured to generate sufficient ozone to kill the selected contaminants in the selected space. In one example, available information indicates that a suitable ozone generator is configured to generate or dose up to about 1 gram ozone per hour (in other cases, up to about 10 grams per hour) in order to provide and maintain an ozone concentration of up to about 20 ppm and, in some cases, about 1 to about 10 ppm ozone. It will be appreciated, however, that the dosing rate and concentration may vary depending on many factors as needed for a particular application.

In principle, it is believed that the level of ozone generation can be affected by the amount and flow of air through the ozone generator 6. By one approach, as shown in FIG. 11, a corona generator 60 is positioned within the ozone generator in an arrangement to provide multi-directional air flow 72 into and through the generator 60. In this manner, it is believed that such multi-directional air flow 72 helps keep the cells 62 cool and helps remove ozone from the space 70 thereby, in principle, permitting additional ozone to be generated in a more efficient manner. While not wishing to be limited by theory, such multi-directional air flow can, in principle, double the ozone output of the generator 60. For example, available information suggests that such a multi-direction air flow through the ozone generator can provide about 50 to about 75 percent higher output of ozone from a plasma ozone generator.

The sterilized air containing ozone is then re-circulated back into the environment and through the above-described blower system 7. The room air 11 is re-circulated or drawn back into the sterilization system 20 to destroy additional airborne contaminants, including those which have been newly introduced into the enclosed area.

Once the sterilization system has performed the desired sterilization, the ozone generator 6 is shut off and the air valve 3 diverts air circulating through the system 20 to the ozone removal zone 4, before the de-ozonated air is re-circulated to the surrounding environment. The de-ozonation 4 is preferably performed until the ozone concentration is reduced to a sufficiently low level to make the area safe for inhabitants. By one approach, such level is about 0.1 ppm or less. Depending on the starting ozone concentration, the ozone removal zone 4 is configured to remove ozone to the low levels (i.e., about 0.1 ppm or less) in about 2 hours or less, preferably about 1 hour or less, and, in some cases, about 30 minutes or less. The mobile system 20 is advantageous, therefore, because downtime of the room, such as a hospital room, with high levels of ozone is minimized. The hospital room, for instance, can be sterilized and turned around for a new patient in a short amount of time using the system 20.

The ozone level can be monitored by sensors within the sterilization system as well as by ozone sensors exposed to the surrounding environment. FIG. 3 shows an exemplary sensor 30. Sensor 30 can be used for controlling an aspect of the operation of the sterilization system. The ozone sensor(s) 30 can be coupled to the programmable logic controller 15, or other suitable means. The sensor(s) 30 can determine the ozone concentration and thus can be suitably employed to determine whether to maintain ozone generation, whether to continue de-ozonation, and to increase or decrease the ozone dosing amount. The ozone generator 6 can, if desired, include a timer, or can be controlled by the programmable logic controller 15 for the sterilization system 20. It will be appreciated that the system 20 can, if desired, be manually controlled.

FIG. 3 is a top view showing the intake filter 1 and air circulation around the UV source (UV devices 2) and the meandering air flow around the baffles 13 before entering an ante chamber 31 having the sensor 30. The sensor 30 can be a suitable sensor board, including a mini-fan, logic means, and the like, as will be apparent to those skilled in the art from this description. Due to the cut-away aspect of FIG. 3, it will be appreciated that element 16 is not depicted. In practice, there may be top support plate extending across the interior side walls and UV elements 2 can depend from such support plate within the air flow around the baffles 13 shown in FIG. 3. The support plate allows the UV light source 2 to be physically held in place and allows electrical wiring for the array to be above the plate and shielded from UV light (and perhaps ozone) when the sterilization system 20 is operational. As will be appreciated, the support plate, interior side walls of the sterilization system will define the interior chamber 12 configured to allow the air to circulate past and be exposed to light generated by the UV generating elements 2.

Figure 4:
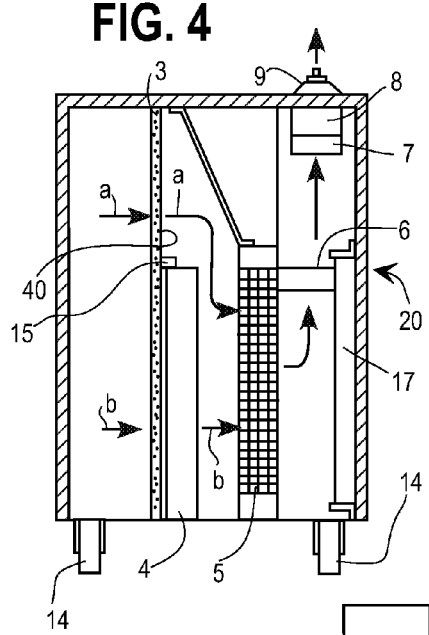
FIG. 4 is a cross section along a vertical axis of an embodiment of an exemplary sterilizer system.

FIG. 4 shows an end view of the exemplary sterilization system 20 in which front panel(s) is removed. The system 20 may include the element 15, which is a member that connects the de-ozonator 4 in sealing abutting engagement to the back side of plate 40. Element 16 is a solid deflector member in this embodiment so that air from ozonation path "a" is directed towards filter 5. Element 16 also serves to separate the ozone destruction zone 4 from filter 5. Element 17 is an electrical panel in this embodiment. Electrical ballast can be mounted to element 17 as can ozone generator 6. As shown, the ozone generator 6 is mounted so as to maximize air flow around and through it so that the circulating air flow may cool the device as discussed previously. Element 16 keeps the air flow to filter 5 regardless of whether air circulation is by either ozonation path "a" or ozone removal path "b". An air valve 3 is shown in side-view and will divert the air to path "a" or to path "b", but not both during the operation of sterilization system 20.

Nozzle 9 can include a butterfly or other valving mechanism to control the flow of air. A shut off valve system can also prevent particulates from falling into the sterilization system when it is not in use, or is being moved from one location to another.

In FIG. 2, a controller is not illustrated although it will be apparent to the person skilled in the art that a controller means, such as the programmable logic controller 15, can control the elements shown, and is preferably capable of receiving program direction from user inputs to control the operation of the sterilization system.

The present sterilization system 20 can be transported to any enclosed area requiring the destruction of bacteria, viruses and odors. For extremely large areas, two or more sterilization systems may be required and can operate concurrently. The present sterilization system 20 can be on wheels 14 to facilitate its being moved from one enclosed area to another, or moved into a storage compartment. However, other modes of transport may also be used such as, but not limited to, rails, guides, slides, castors, ramps, tracks, and the like. Transportable generally refers to a system that is configured and arranged and has a size and weight such that it can be moved by an individual of average size and weight, such as by pushing or carrying from room to room. It will be appreciated that the present invention can be applied to such systems as are described in U.S. Patent Application Publication US 2005/0186108A1, and that the present sterilization system 20 can be incorporated into a mobile medical unit, such as a mobile medical unit described in U.S. Pat. No. 4,915,435, the complete disclosures of which are incorporated herein by reference.

The system 20 also includes a method of measuring and controlling the application of ozone to sterilize a space using a controller with ozone sensing and the monitoring of various environmental parameters or combinations thereof. The methods herein permit the ozone sterilizing process to sterilize the offending agents in a consistent manner because a variety of parameters are selected, monitored, and/or controlled. It will be appreciated that various environmental variations, such as, but not limited to the following characteristic in the space to be sterilized can affect the sterilization process: room volume, materials present within the room (both solid and vapor), room's leakage rates, temperature, barometric pressure, and other psychrometric parameters.

The system 20, therefore, can measure any or all of a variety of psychrometric parameters so that the optimum dosage required to sterilize the room can be determined. The controller 15 can then assure that the proper dosing of the room is accomplished. The controller can also store a data base of dosages for each agent to be sterilized, such as various kinds of bacteria, viruses, mold or fungi installed in a data base along with dosage requirements to inactivate or kill such agents. The user of the controller 15 can then select the particular agent or agents that they wish to remove, and the machine will analyze and decide on the proper dosage requirement for the room. The dosing rate of microorganisms varies as a function of many environmental parameters and the data base will use this information to set the controller's dosage rate.

The system 20 can also estimate the amount of residual dosage that is present in the room's atmosphere prior to the time the controller switches processes and begins removing ozone. In principle, this residual ozone represents an additional source of ozone that is effective in room sterilization and is not typically counted in the room dosage. By using this residual ozone, the controller can minimize the overall time that the room is under sterilization.

For purposes herein, the ozone dosage can be calculated using a value known as a "Cleo". The total "Cleos" represent the total sterilization value of ozone applied to the room. The Cleo Unit represents concentration of ozone per unit time and is typically measured and calculated from parts per million of ozone multiplied by the minutes of ozone exposure. The unit of a Cleo, therefore, is used to convey this value and typically has units of parts per million-minutes (ppm-min). While a Cleo unit will vary based on many factors (i.e., contaminant, pathogen, room size, temperature, humidity, etc.), exemplary ranges can be from about 300 to about 1000 ppm-minute. Such Cleo values are suitable in many cases to kill about 99.9 percent Staphylococcus aureus. Since the concentration of ozone continuously varies during the sterilization process, the methods herein permit the monitoring and control of the ozone dosing to enable determination and varying the ozone dosing respondent to the measured parameters (such as ozone concentration and various environmental parameters).

The controller not only measures psychrometric parameters, but it preferably can also control such parameters, such as, but not limited to, temperature and humidity within a room. For example, while not wishing to be limited by theory, it is believed in principle that lower temperatures, high pressures, and high relative humidity are more effective in killing organisms and other contaminants with ozone. For example, it is believed that at least about 50 percent and, in some cases, about 50 percent to about 75 percent (or higher) relative humidity is more effective in ozone sterilization. As a result, the methods herein can measure room relative humidity and, if needed, add (or remove) moisture to desired levels for most efficient sterilization. In addition, it is believed that temperatures of about 12 to about 18° C. are more effective in generating sufficient quantities of ozone needed to sterilize the enclosed space. As a result, the methods herein can also measure room temperature and, if needed, increase (or decrease) the temperature to desired ranges. By one approach, the method can continuously monitor and measure the environmental parameters. While the above describes exemplary environmental parameters, it will be appreciated that such parameters may vary depending on the particular agent to be sterilized, room size, and other parameters.

Alternatively, the method may also vary the dosing amount to take into the environmental parameters. That is, the dosing amount or duration can vary respondent to the various measured environmental parameters. For example, with a lower pressure or lower relative humidity, increased dosage rates may be used. For higher temperatures, increase application durations may be used.

The machine or controller will calculate the ozone dose to match a user applied setting based on the measured parameter(s) and selected agents. Dosing also allows the user to minimize the time to sterilize a room by taking advantage of total ozone resident in room throughout the sterilizing and the residual ozone present in the ozone reduction process. This is accomplished by predicting the total application time and adding to it the predicted amount of ozone resident during the ozone reduction process.

The exact calculation of the Cleo unit generally involves using the instantaneous measurement of ozone concentration in the room and aggregating or integrating it as a function of time. Alternatively, other less accurate methods of estimating the ozone dosage, may also be applied. During a typical ozone cleansing cycle, the ozone dosing calculation may be arrived at by measuring the ozone density in parts per million every minute and multiplying the value by one minute (other time intervals may also be used). The resulting quantity would then be summed with the next dosing value, which calculated value would closely approximate the actual integration of the ozone concentration versus time curve. As a result, the ozone management system 20 preferably continuously monitors and projects the amount of ozone required to dose and kill the bacteria within a room based on the particular agent selected and various environmental parameters measured.

Advantages and embodiments of the concentrates described herein are further illustrated by the following examples; however, the particular conditions, flow schemes, materials and amounts thereof recited in these examples, as well as other conditions and details, should not be construed to unduly limit this method. All percentages are by weight unless otherwise indicated.

EXAMPLES

Example 1

A study was completed to measure ozone concentration and temperature over time in an enclosed chamber of about 2,000 ft$^3$ (200 ft$^2$ chamber having a 10 foot high ceiling). The chamber was sealed from air entering or leaving the chamber and fabricated out of walls made from polyethylene.

An ozone generating element (Plasma Technologies Inc., Racine, Wis.) was placed in the enclosed chamber and an ozone sensor (Aerogual Ltd., Auckland, New Zealand) measured the amount of ozone in the chamber over time. A temperature sensor also concurrently measured the chamber air temperature. A plot of ozone concentration and temperature over time is provided in FIG. 12. Ozone was supplied at a rate of about 1 gram/hour.

Figure 12:
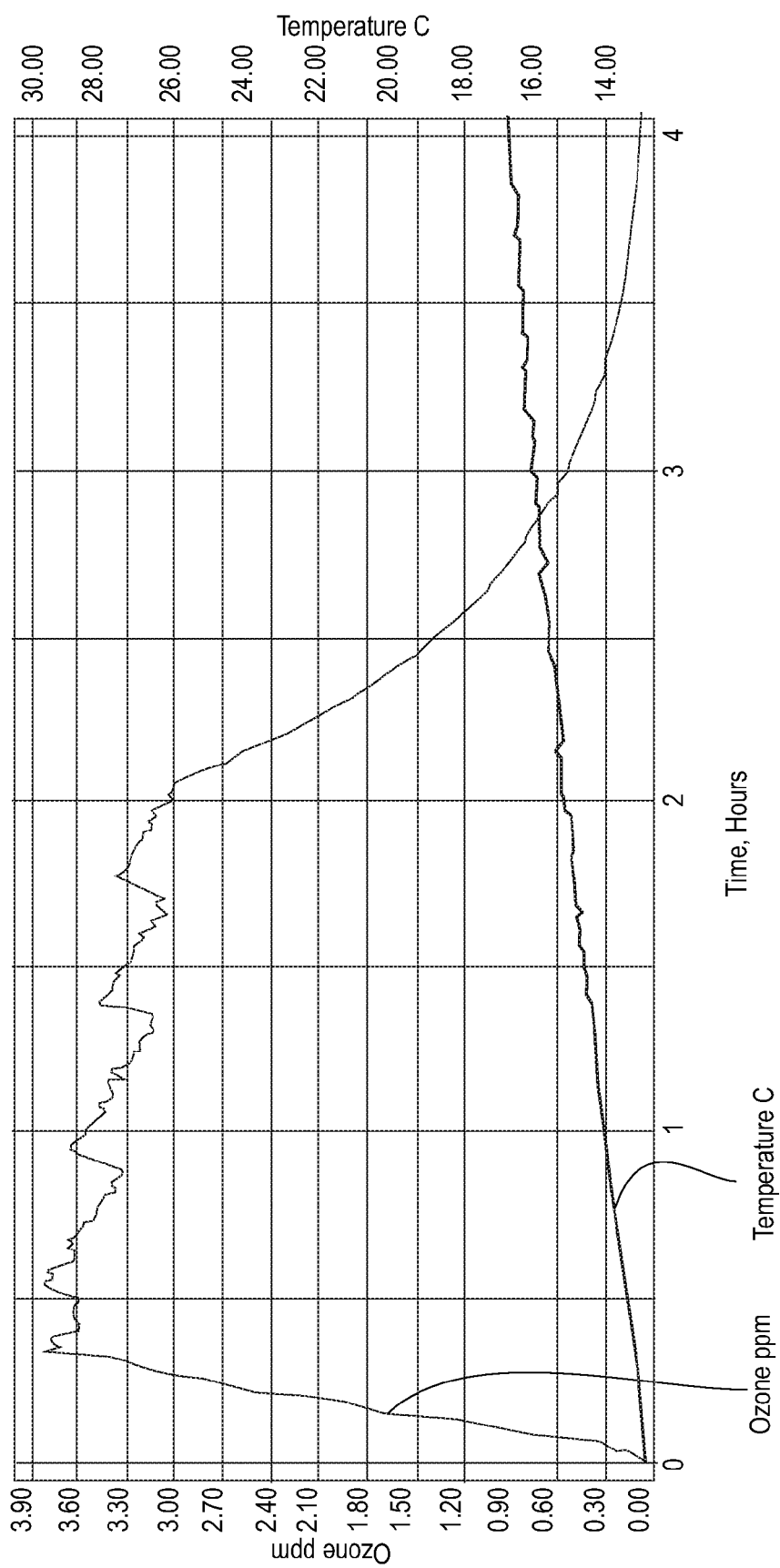
FIG. 12 is a plot of ozone concentration and temperature as a function of time.

As shown in FIG. 12, the ozone concentration reached about 3 to about 4 ppm in about 15 minutes after ozone dosing commenced. After about 2 hours of ozone dosing, the ozone generator was turned off and an ozone removal zone was activated. Ozone was removed with a manganese oxide catalyst. After about 2 hours, the amount of ozone in the enclosed chamber was reduced to about 0.09 ppm.

Example 2

A study was completed using an exemplary sterilization system as described herein using only the UV light source to kill airborne pathogens. A mixture of about 2500 to about 2600 CFU (colony forming units) of Mycobacterium smegmatis (a tuberculous surrogate) was sprayed at the intake of the system. The system was then operated at about 96 CFM and only the UV light source irradiated the air flow at about 254 nanometers. At the output nozzle of the system, there were zero recorded CFUs. Samples were analyzed by Aerobiology Laboratory, Dulles, Va.).

Example 3

A study was completed to determine the ability of the sterilization systems described herein to kill pathogens using ozone. In one study, cultures containing about 7380 CFUs (culture forming units) of *Acinetobacter baumanii* were placed in an enclosed room of about 2000 ft$^3$ of about 70° F. and about 50 percent relative humidity. The sterilization system supplied about 5 ppm of ozone to the room from an ozone generating unit (Plasma Technologies). After about 2 hours of dosing, the culture had about 0 CFUs. In another study, cultures containing about 7900 CFUs of *Aspergillius fumigatus* were placed in an enclosed room of about 2000 ft$^3$ at about 70° F. and about 50 percent relative humidity. The sterilization system supplied about 5 ppm of ozone to the room. After about 2 hours of dosing, the culture had about 20 CFUs. Testing was completed at Aerobiology Laboratory Example 4

Figure 13:
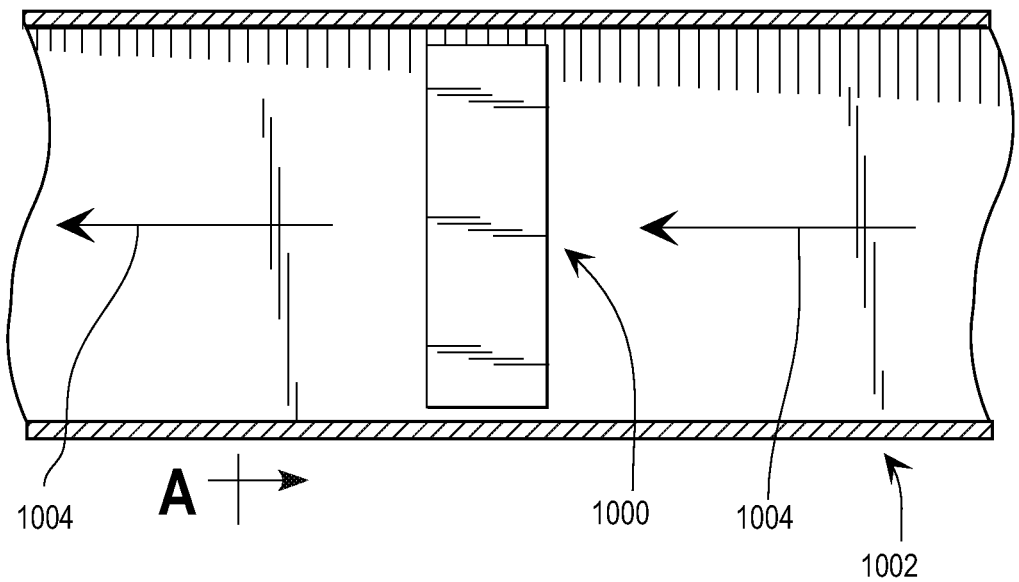
FIG. 13 is a cross-sectional side view showing a comparative configuration for an ozone generating element.

A study was completed to determine the effect of air flow on the ability of an ozone generator to provide ozone. In a comparative configuration, an ozone generating element 1000 (Plasma Technologies) was placed in a plenum 1002 as generally illustrated in FIG. 13 so that air 1004 can only flow in a single direction (i.e., uni-directional air flow) through the ozone generator. The configuration of FIG. 13 was capable of providing about 0.6 grams of ozone per hour, with about 96 CFM air flow rate in a plenum of about 16 in$^2$. Ozone concentration was measured downstream of the generating element 1000.

Figure 14:
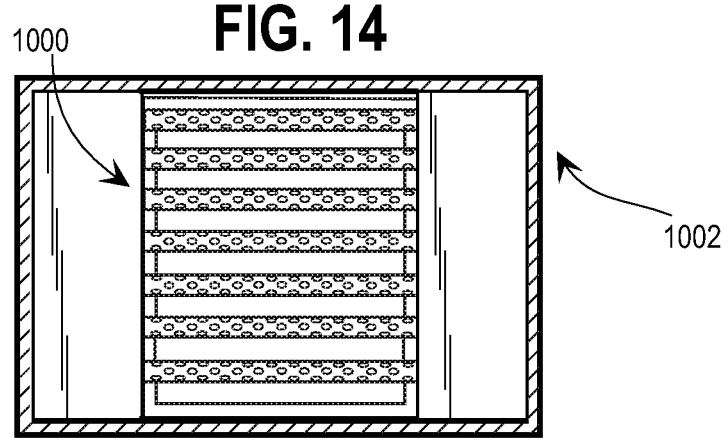
FIG. 14 is a rear elevational view generally along lines A-A of the exemplary ozone generating element of FIG. 13.
Figure 15:
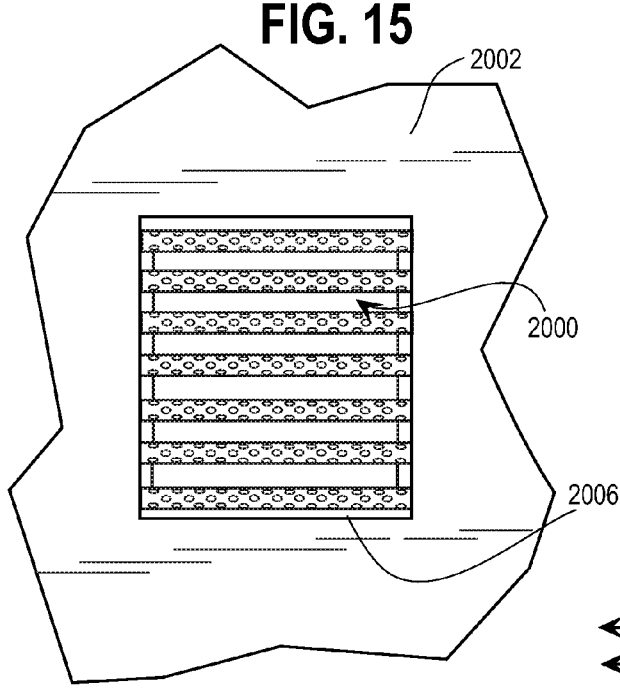
FIG. 15 is a rear elevational view of an exemplary inventive configuration for an ozone generating element.
Figure 16:
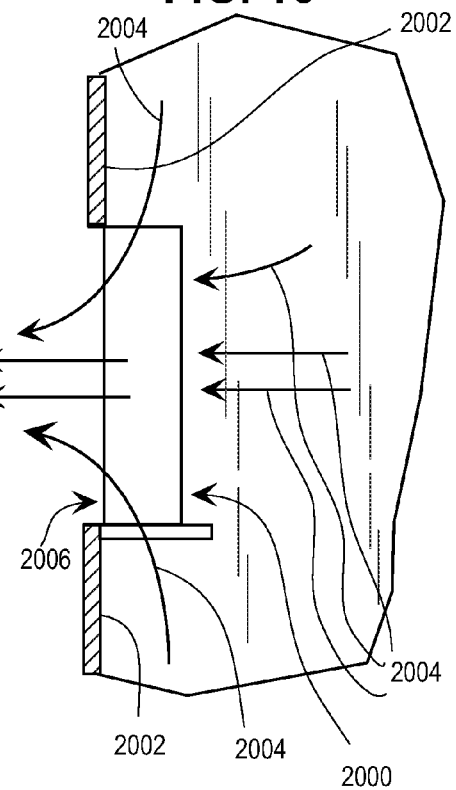
FIG. 16 is a cross-sectional side view of the exemplary inventive configuration of FIG. 15.
Figure 17:
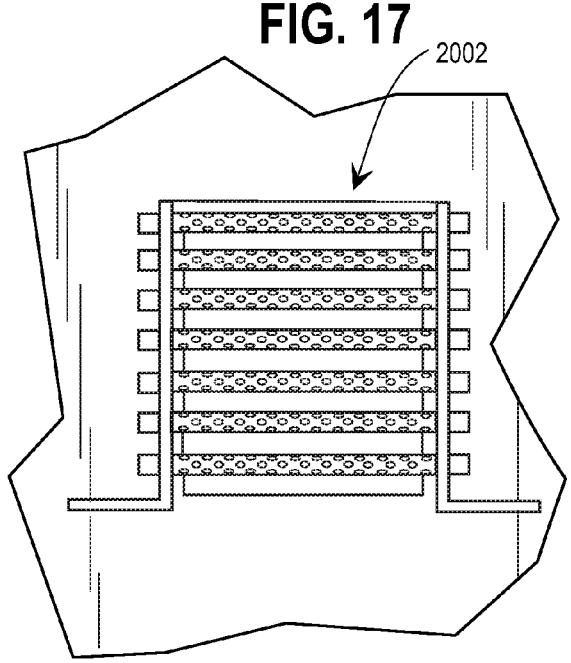
FIG. 17 is a front elevational view of the exemplary inventive configuration of FIG. 15.

In one exemplary inventive configuration, an ozone generator 2000 (Plasma Technologies) was placed on a mounting panel 2002 so that a multi-directional air flow 2004 could flow through the ozone generator and then be concentrated through a narrowed orifice 2006 in the mounting panel 2002 at the downstream end of the ozone generator 2000 as generally illustrated in FIG. 14. The orifice 2006 has a cross-sectional area of about 8 in$^2$. The configuration of FIG. 14 was capable of providing about 0.9 grams of ozone per hour, which is an improvement over the configuration of FIG. 13 of about 50 percent. It is believed that even greater increases (up to about 75 percent or more) are also possible. Air flow rate was about 96 CFM and the plenum in this case had a cross-sectional area of about 64 in$^2$.

While not wishing to be limited by theory, it is believed that the multi-directional air flow through the generator and the use of the downstream orifice imparts a shearing and/or turbulence on the air flow through the generator along with, in principle, a pressure drop and velocity increase of the air. As a result, it is believed that the generated ozone can be removed from the ozone generator at a faster rate thereby allowing fresh oxygen to be drawn into the generator and converted to ozone.

It will be understood that various changes in the details, materials, and arrangements of the methods, processes, and systems, which have been herein described and illustrated in order to explain the nature of the system and methods therein, may be made by those skilled in the art within the principle and scope of the embodied method as expressed in the appended claims.

What is claimed is:

1. A method of measuring and controlling the application of ozone to sterilize a predetermined space, the method comprising:

measuring an environmental parameter of the predetermined space, the environmental parameter including temperature, relative humidity, pressure, dew point, or combinations thereof;

selecting a contaminant for sterilization, the contaminant selected from the group consisting of bacteria, virus, mold, fungi, and combinations thereof;

determining a minimum ozone dosage and minimum ozone application duration sufficient to inactivate the selected contaminant, the ozone dosage and the ozone application duration dependant on the measured environmental parameter and the contaminant selected for sterilization;

determining a concentration of ozone per unit time sufficient to inactivate the selected contaminant dependant on the minimum ozone dosage and minimum ozone application duration;

supplying ozone to the predetermined space from an ozone generator, the supplied ozone in an amount sufficient to generally achieve the determined concentration of ozone per unit time;

monitoring ozone concentration in the predetermined space;

monitoring the ozone concentration at a predetermined interval; and aggregating the monitored ozone concentrations at each predetermined interval to determine an overall ozone concentration.

2. The method of claim 1, wherein the ozone is supplied in an amount up to about 10 grams per hour.

3. The method of claim 1, wherein the supplied ozone is sufficient to provide up to about 20 ppm ozone in the predetermined space having an air volume of about 1000 $ft^3$ or larger.

4. The method of claim 1, further comprising adjusting the amount of ozone supplied responsive to the monitored ozone concentration.

5. The method of claim 1, further comprising adjusting the ozone application duration responsive to the monitored ozone concentration.

6. The method of claim 1, wherein after the ozone application duration has elapsed, stopping supplying ozone to the predetermined space and measuring a residual concentration of ozone in the predetermined space.

7. The method of claim 6, wherein after the ozone application duration has elapsed, removing ozone from the predetermined space.

8. The method of claim 6, further comprising after the ozone application duration has elapsed, diverting air from the predetermined space to an ozone removal zone for removal of the ozone from the predetermined space.

9. The method of claim 1, further comprising after measuring the environmental parameter, adjusting the environmental parameter.

10. The method of claim 9, wherein adjusting the environmental parameter includes adding or removing moisture from the predetermined space to control relative humidity.

11. The method of claim 10, wherein the relative humidity is controlled to a predetermined range based on the selected contaminant.

12. The method of claim 9, wherein adjusting the environmental parameter includes increasing or decreasing a temperature of the predetermined space.

13. The method of claim 12, wherein the temperature is controlled to a predetermined range based on the selected contaminant.

14. The method of claim 1, wherein the environmental parameter is measured at a predetermined interval throughout the ozone application duration.

* * * * *